US00PP12789P2

(12) United States Plant Patent
Glicenstein

(10) Patent No.: US PP12,789 P2
(45) Date of Patent: Jul. 23, 2002

(54) CHRYSANTHEMUM PLANT NAMED 'YOTRENTON'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/594,753

(22) Filed: Jun. 16, 2000

(51) Int. Cl.[7] ..... A01H 5/00

(52) U.S. Cl. ..... Plt./288

(58) Field of Search ..... Plt./288

(56) References Cited

PUBLICATIONS

UPOV–ROM, 2001/03, Plant Variety Database, GTI Jouve Retrieval Software, citation for 'Yotrenton'.*
Copy of front page of EU5693, dated Dec. 20, 1999.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yotrenton', characterized by its upright, outwardly spreading, compact and uniformly mounded plant habit; dense and full plants; uniform flowering response; early flowering, eight-week response time; large decorative-type inflorescences that are about 9.8 cm in diameter; excellent inflorescence form retention; white-colored ray florets; and good postproduction longevity with inflorescences maintaining good substance and color for about three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Yotrenton.

The new Chrysanthemum is a product of a planned breeding program conducted by the Inventor in Salinas, Calif. The objective of the breeding program is to create new potted Chrysanthemum cultivars with desirable inflorescence form and floret colors and good postproduction longevity.

The new Chrysanthemum originated from a cross made by the Inventor in December, 1993, in Salinas, Calif., of a proprietary Chrysanthemum seedling selection identified as YB-4149 as the female, or seed, parent with the Chrysanthemum cultivar Claro, disclosed in U.S. Plant Pat. No. 6,946 as the male, or pollen parent. The new Chrysanthemum was discovered and selected by the Inventor in May, 1995, as a single flowering plant within the progeny of the stated cross grown in a controlled environment in Salinas, Calif. The selection of this plant was based on its desirable inflorescence form and floret colors and good postproduction longevity.

Asexual reproduction of the new Chrysanthemum by vegetative tip cuttings was first conducted in Salinas, Calif. in July, 1995. Asexual reproduction by cuttings has shown that the unique features this new Chrysanthemum are stable and reproduced true to type in successive generations.

SUMMARY OF THE INVENTION

The cultivar Yotrenton has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yotrenton'. These characteristics in combination distinguish 'Yotrenton' as a new and distinct Chrysanthemum:

1. Upright, outwardly spreading, compact and uniformly mounded plant habit.
2. Dense, full plants.
3. Uniform flowering response.
4. Early flowering, eight-week response time.
5. Large decorative-type inflorescences that are about 9.8 cm in diameter; excellent inflorescence form retention.
6. White-colored ray florets.
7. Good postproduction longevity with inflorescences maintaining good substance and color for about three weeks in an interior environment.

Plants of the new Chrysanthemum are more uniform in plant habit and flowering than plants of the female parent, the cultivar Claro. Plants of the new Chrysanthemum and the male parent, the selection YB-4149, differ primarily in ray floret coloration.

Plants of the new Chrysanthemum differ from plants of the cultivar, White Diamond, disclosed in U.S. Plant Pat. No. 8,059, in the following characteristics:

1. Inflorescence form of plants of the new Chrysanthemum is more formal and tidier than inflorescence form of plants of the cultivar White Diamond.
2. Plants of the new Chrysanthemum have smaller inflorescences than plants of the cultivar White Diamond.
3. Ray floret color of plants of the new Chrysanthemum is more white than ray floret color of plants of the cultivar White Diamond.

4. Foliage of plants of the new Chrysanthemum is stronger and less likely than plants of the cultivar White Diamond to break down under low light production conditions.
5. Plants of the new Chrysanthemum have stronger stems than plants of the cultivar White Diamond.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Yotrenton'.

The photograph at the bottom of the sheet comprises a close-up view of typical inflorescences of the cultivar Yotrenton.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbud-types. Measurements and numerical values represent averages of typical flowering plants.

Botanical classification: *Dendranthema grandiflora* cultivar Yotrenton.

Commercial classification: Decorative-type potted Chrysanthemum.

Parentage:

*Female, or seed, parent.*—Proprietary Chrysanthemum seedling selection identified as YB-4149.

*Male, or pollen, parent.*—*Dendranthema grandiflora* cultivar Claro, disclosed in U.S. Plant Pat. No. 6,946.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative-type potted Chrysanthemum that can be grown as a disbud or spray-type, but typically grown as a disbud-type. Compact; inverted triangle; stems upright and outwardly spreading giving a uniformly mounded appearance to the plant. About three lateral branches develop after removal of terminal apex (pinching); full and dense plants. Moderate vigor.

*Plant height.*—About 20 cm.

*Plant width.*—About 32 cm.

*Lateral branches.*—Length: About 11 cm. Diameter: About 4 mm. Internode length: About 1.3 cm. Strength: Flexible, but strong. Texture: Pubescent. Color: 146A.

*Foliage description.*—Arrangement: Alternate. Length: About 6.5 cm. Width: About 4.5 cm. Apex: Sharply acute. Base: Attenuate. Margin: Palmately lobed, sinuses between lateral lobes mostly divergent. Texture: Upper and lower surfaces with very fine pubescence; veins prominent on lower surface. Color: Young foliage upper surface: 147A. Young foliage lower surface: 147B. Mature foliage upper surface: 147A. Mature foliage lower surface: 147B. Venation upper surface: 147A to 147B. Venation lower surface: 147B. Petiole length: About 2.1 cm. Petiole diameter: About 2.5 mm. Petiole color: 147B.

Inflorescence description:

*Appearance.*—Decorative-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for about three weeks in an interior environment.

*Quantity of inflorescences.*—Can be grown as a disbud or spray-type, however, typically grown as a disbud-type with one inflorescences per lateral stem; about three inflorescences per plant.

*Inflorescence bud.*—Height: About 6 mm. Diameter: About 8 mm. Color: More green than 147A.

*Inflorescence size.*—Diameter: About 9.8 cm. Depth (height): About 3.2 cm. Diameter of disc: About 4 mm, inconspicuous. Receptacle diameter: About 7 mm.

*Ray florets.*—Shape: Elongated-oblong. Orientation/aspect: Initially incurved, outer rows opening to perpendicular to stem; initially concave then becoming convex with development. Length: About 4.8 cm. Width: About 1.5 cm. Apex: Acute or emarginate. Base: Attenuate; short to medium corolla tube. Margin: Enitre. Texture: Smooth, glabrous, satiny. Number of ray florets per inflorescence: About 147. Color: When opening, upper surface: 155D. When opening, lower surface: 155D. Fully opened, upper surface: 155D. Fully opened, lower surface: 155D.

*Disc florets.*—Shape: Tubular, flared. Apex: Five-pointed. Length: About 6 mm. Width: Apex, about 1.5 mm; base, about 1 mm. Number of disc florets per inflorescence: Less than 20, inconspicuous. Color: Immature: 144A. Mature: Apex: 5A. Mid-section: Very light green, close to 154C. Base: White.

*Reproductive organs.*—Androecium: Present on disc florets only. Anther color: 9A. Pollen amount: None observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yotrenton', as illustrated and described.

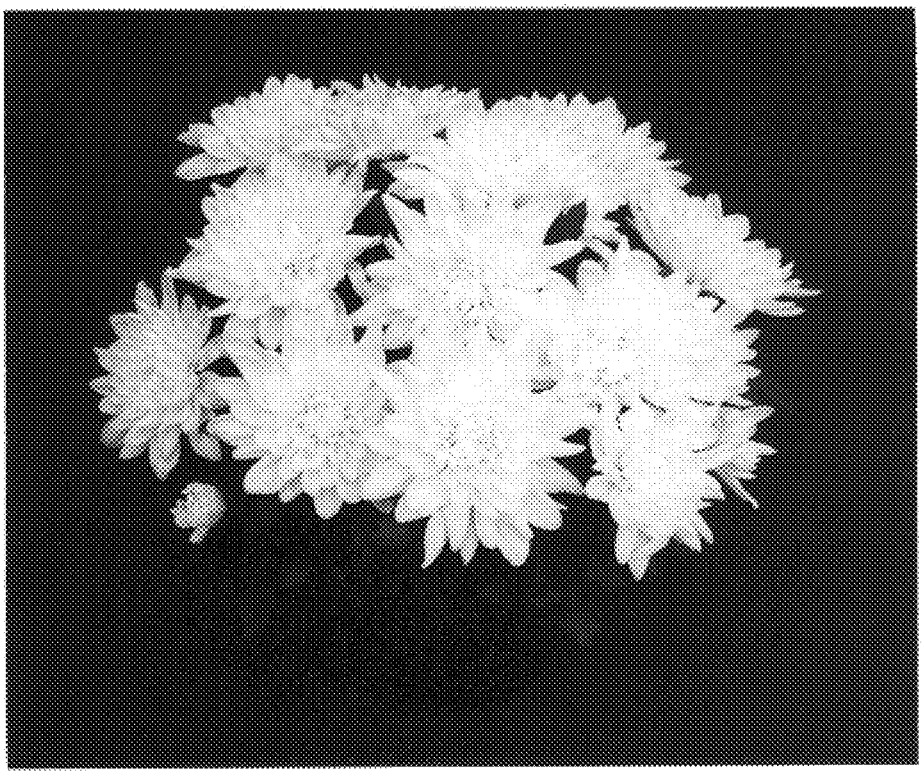
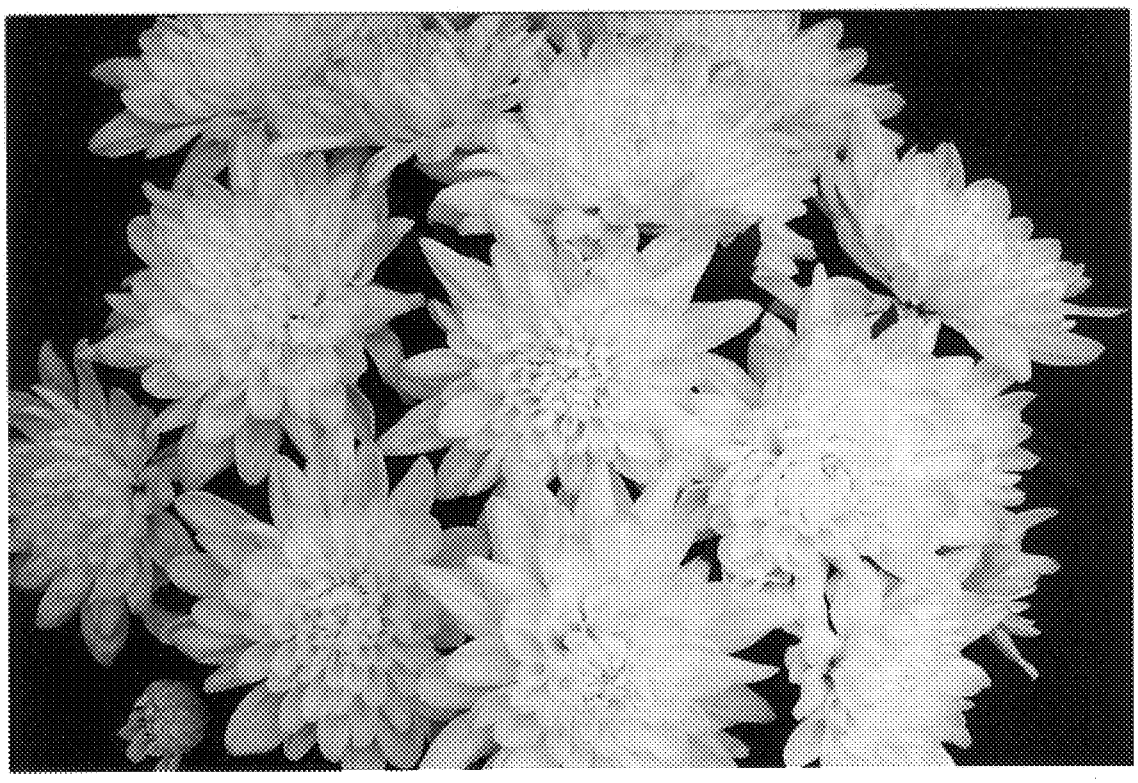

* * * * *